(12) United States Patent
Sanders et al.

(10) Patent No.: US 7,045,324 B2
(45) Date of Patent: May 16, 2006

(54) TOCOPHEROL ASSOCIATED PROTEIN AND USES THEREOF

(75) Inventors: Bob G. Sanders, Austin, TX (US); Kimberly Kline, Austin, TX (US); Weiping Yu, Austin, TX (US); Hui Liu, Houston, TX (US); Feras Hantash, Dana Point, CA (US)

(73) Assignee: Research Development Foundation, Carson City, NV (US)

( * ) Notice: Subject to any disclaimer, the term of this patent is extended or adjusted under 35 U.S.C. 154(b) by 317 days.

(21) Appl. No.: 10/419,629

(22) Filed: Apr. 21, 2003

(65) Prior Publication Data

US 2004/0023915 A1 Feb. 5, 2004

Related U.S. Application Data

(60) Provisional application No. 60/373,870, filed on Apr. 19, 2002.

(51) Int. Cl.
- C12N 9/02 (2006.01)
- C12N 1/20 (2006.01)
- C12N 15/00 (2006.01)
- C07K 1/00 (2006.01)
- C07H 21/04 (2006.01)

(52) U.S. Cl. ............... 435/189; 435/4; 435/6; 435/252.3; 435/320.1; 435/252.8; 435/440; 536/23.2; 536/23.7; 536/23.4; 530/350

(58) Field of Classification Search .............. 435/183, 435/4, 6, 252.3, 320.1, 252.8, 440, 23.2, 435/23.4; 530/350; 536/23.7, 23.2, 23.4
See application file for complete search history.

(56) References Cited

U.S. PATENT DOCUMENTS

| 2004/0023915 A1 | 2/2004 | Sanders et al. ............... 514/44 |
| 2004/0152883 A1 | 8/2004 | Sanders et al. ............ 536/23.2 |

OTHER PUBLICATIONS

Current Protocols in Molecular Biology. John Wiley & Sons, Inc. 1998. Unit 1.5.*
Current Protocols in Molecular Biology. John Wiley & Sons, Inc. 1996. Unit 20.2.*
Dutta-Roy et al., "Purification and partial characterisation of an alpha-tocopherol-binding protein from rabbit heart cytosol," Mol. Cell. Biochem. 123:139-144, 1993.

(Continued)

Primary Examiner—Manjunath Rao
Assistant Examiner—Yong D. Pak
(74) Attorney, Agent, or Firm—Fulbright & Jaworski L.L.P.

(57) ABSTRACT

The present invention provides a novel tocopherol associated protein (TAP-38) DNA/protein with a 76 nucleotide base deletion resulting in a 25 amino acid deletion, followed by 90 novel nucleotides that code for 30 novel amino acids that are not expressed by TAP-46. The present invention provides data showing that TAP-38 enhances the apoptotic inducing properties of tocopherol based compounds, and blockage of TAP reduces the effectiveness of tocopherol based compounds. Thus, the present invention claim that expression of TAP-38 by tumor cells enhances the apoptotic inducing properties of tocopherol based compounds. The present invention provides aerosol liposome/transfection/infection methods for delivery of TAP-38 and TAP-46 cDNA plasmids separately and in combination with tocopherol based apoptotic inducing agents as well as with other chemotherapeutic agents as a method for treatment and prevention of cellular proliferative diseases and disorders.

12 Claims, 12 Drawing Sheets

```
  1 atgagcggca gagtcggcga tctgagcccc aggcagaagg aggcattggc caagccagaa
 61 gcttcgacct gcagaagtcg gaggccatgc tccggaagca tgtggagttc cgaaagcaaa
121 aggacattga caacatcatt agcatggcag cctccagagg tgatccaaca gtatctgtca
181 gggggtatgt gtggctatga cctggatggc tgcccagtct ggtacgacat aattggacct
241 ctggatgcca agggtctgct gttctcagcc tccaaacagg acctgctgag gaccaagatg
301 cgggagtgtg agctgcttct gcaagagtgt gcccaccaga ccacaaagtt ggggaggaag
361 gtggagacca tcaccataat ttatgactgc gaggggcttg gcctcaagca tctctggaag
421 cctgctgtgg aggcctatgg agagtttctc tgcatgtttg aggaaaatta tcccgaaaca
481 ctgaagcgtc tttttgttgt taaagccccc aaactgtttc ctgtggccta taacctcatc
541 aaaccctcc tgagtgagga cactcgtaag aagatcatgg tcctgggagc aaattggaag
601 gaggttttac tgaaacatat cagccctgac caggtgcctg tggagtatgg gggcaccatg
661 actgaccctg atggaaaccc caagtgcaaa tccaagatca actacgggg tgacatcccc
721 aggaagtatt atgtgcgaga ccaggtgaaa cagcagtatg aacacagcgt gcagatttcc
781 cgtggctcct cccaccaagt ggagtatgag atcctcttcc ctggctgtgt cctcaggtgg
841 cagtttatgt cagatggagc ggatgttggt tttgggattt tcctgaagac caagatggga
901 gagaggcagc ggcagggga gatgacagag gtgctgccca accagaggta caactcccac
961 ctgtccctg aagatgggac cctcacctgc agtgatcctg gcatctatgt cctgcggttt
1021 gacaacacct acagcttcat tcatgccaag aaggtcaatt tcactgtgga ggtcctgctt
1081 ccagacaaag cctcagaaga gaagatgaaa cagctggggg caggcacccc gaaataa
```
(SEQ ID NO: 1)

OTHER PUBLICATIONS

Dutta-Roy et al., "alpha-tocopherol-binding proteins: purification and characterization," *Methods Enzymology*, 282:278-297, 1997.

Gordon et al., "Characterization of a novel alpha-tocopherol-binding protein from bovine heart cytosol," *Arch. Biochem. Biophys.*, 318:140-146, 1995.

Sha et al., "Crystal structure of the Saccharomyces cerevisiae phosphatidylinositol-transfer protein," *Nature*, 391:506-510, 1998.

Shibata et al., "Supernatant protein factor, which stimulates the conversion of squalene to lanosterol, is a cytosolic squalene transfer protein and enhances cholesterol biosynthesis," *Proc. Natl. Acad. Sci.* USA, 98:2244-2249, 2001.

Stocker et al., "Identification of a novel cytosolic tocopherol-binding protein: structure, specificity, and tissue distribution," *IUBMB Life*, 48:49-55, 1999.

Zimmer et al., "A novel human tocopherol-associated protein: cloning, in vitro expression, and characterization," *J. Biol. Chem.*, 275:25672-25680, 2000.

* cited by examiner

```
   1 atgagcggca gagtcggcga tctgagcccc aggcagaagg aggcattggc caagccagaa
  61 gcttcgacct gcagaagtcg gaggccatgc tccggaagca tgtggagttc cgaaagcaaa
 121 aggacattga caacatcatt agcatggcag cctccagagg tgatccaaca gtatctgtca
 181 gggggtatgt gtggctatga cctggatggc tgcccagtct ggtacgacat aattggacct
 241 ctggatgcca agggtctgct gttctcagcc tccaaacagg acctgctgag gaccaagatg
 301 cgggagtgtg agctgcttct gcaagagtgt gcccaccaga ccacaaagtt ggggaggaag
 361 gtggagacca tcaccataat ttatgactgc gaggggcttg cctcaagca tctctggaag
 421 cctgctgtgg aggcctatgg agagtttctc tgcatgtttg aggaaaatta cccgaaaca
 481 ctgaagcgtc tttttgttgt taaagccccc aaactgtttc ctgtggccta taacctcatc
 541 aaacccttcc tgagtgagga cactcgtaag aagatcatgg tcctgggagc aaattggaag
 601 gaggttttac tgaaacatat cagccctgac caggtgcctg tggagtatgg gggcaccatg
 661 actgaccctg atggaaaccc caagtgcaaa tccaagatca actacggggg tgacatcccc
 721 aggaagtatt atgtgcgaga ccaggtgaaa cagcagtatg aacacagcgt gcagatttcc
 781 cgtggctcct cccaccaagt ggagtatgag atcctcttcc ctggctgtgt cctcaggtgg
 841 cagtttatgt cagatggagc ggatgttggt tttgggattt tcctgaagac caagatggga
 901 gagaggcagc gggcagggga gatgacagag gtgctgccca accagaggta caactcccac
 961 ctggtccctg aagatgggac cctcacctgc agtgatcctg catctatgt cctgcggttt
1021 gacaacacct acagcttcat tcatgccaag aaggtcaatt tcactgtgga ggtcctgctt
1081 ccagacaaag cctcagaaga gaagatgaaa cagctggggg caggcacccc gaaataa
```

(SEQ ID NO: 1)

Fig. 1

MSGRVGDLSPRQKEALAKPEASTCRSRRPCSGSMWSSESKRTLTTSLAWQPPEVIQQYL
SGGMCGYDLDGCPVWYDIIGPLDAKGLLFSASKQDLLRTKMRECELLQECAHQTTKLG
RKVETITIYDCEGLGLKHLWKPAVEAYGEFLCMFEENYPETLKRLFVVKAPKLFPVAY
NLIKPFLSEDTRKKIMVLGANWKEVLLKHISPDQVPVEYGGTMTDPDGNPKCKSKINYG
GDIPRKYYVRDQVKQQYEHSVQISRGSSHQVEYEILFPGCVLRWQFMSDGADVGFIFL
KTKMGERQRAGEMTEVLPNQRYNSHLVPEDGTLTCSDPGIYVLRFDNTYSFIHAKKVNF
TVEVLLPDKASEEKMKQLGAGTPK (SEQ ID NO: 2)

Fig. 2

```
TAP-46  ATGAGCGGCAGAGTCGGCGATCTGAGCCCCCAGGCAGAAGGAGGCATTGGCCAAG
TAP-38  ATGAGCGGCAGAGTCGGCGATCTGAGCCCCCAGGCAGAAGGAGGCATTGGCCAAG

TAP-46  tttcgggagaatgtgtccaggatgtgctgccgaatccagatgactat
TAP-38  ----------------------------------------------

TAP-46  tttctcctgcgttggctccgagCCAGAAGCTTCGACCTGCAGAAGTCGGAGGCC
TAP-38  ---------------------CCAGAAGCTTCGACCTGCAGAAGTCGGAGGCC TAP-46  ATGCTCCGGAAGCATGTGGAGTTCCGAAAAGCAAAAAGGACATTGACAACATCATT
TAP-38  ATGCTCCGGAAGCATGTGGAGTTCCGAAAAGCAAAAAGGACATTGACAACATCATT TAP-46  AGCCT-GGCAGCCTCCAGAGGTGATCCAACAGTATCTGTCAGGGGGTATGTGTGG
TAP-38  AGCATGGCAGCCTCCAGAGGTGATCCAACAGTATCTGTCAGGGGGGTATGTGTGG

TAP-46  (SEQ ID NO: 3)
```

Fig. 3

```
TAP-46   MSGRVGDLSPRQKEALAKFRENVQDVLPALPNPDDYFLLRWLRARSFDLQKSEAMLRKHV
  **             R  R    S      SE
TAP-38   MSGRVGDLSPRQKEALAKPEAST---------------CRSRRPCSGSMWSSES------

TAP-46   EFRKQKDIDNIISWQPPEVIQQYLSGGMCGYDLDGCPVWYDIIGPLDAKGLLFSASKQDL
  **                WQPPEVIQQYLSGGMCGYDLDGCPVWYDIIGPLDAKGLLFSASKQDL
TAP-38   ----KRTLTTSLAWQPPEVIQQYLSGGMCGYDLDGCPVWYDIIGPLDAKGLLFSASKQDL

** Homology
```

Fig. 4

TOCOPHEROL ASSOCIATED PROTEIN AND USES THEREOF

CROSS-REFERENCE TO RELATED APPLICATION

This non-provisional patent application claims benefit of provisional patent applications 60/373,870, filed Apr. 19, 2002, now abandoned.

BACKGROUND OF THE INVENTION

1. Field of the Invention

The present invention relates generally to the fields of molecular genetics, cancer biology, cancer prevention, and cancer chemotherapy. More specifically, the present invention relates to the c-DNA cloning and nucleotide sequencing of a novel tocopherol associated protein, referred to as TAP-38, from human normal and breast cancer cells, and the use of molecular/immune technologies to demonstrate that this protein is relevant to the ability of novel tocopherol compounds to induce cancer cells to undergo growth arrest via inhibition of DNA synthesis, induction of cellular differentiation, and induction of apoptosis.

2. Description of the Related Art

The regulatory controls of pro-life (cell proliferation) and pro-death (apoptosis) are extremely complex and involve multiple intracellular signaling pathways and multiple interacting gene products. Cancer cells may exhibit multiple defects in normal regulatory controls of cell proliferation, such as enhanced expression of genes, which allow them to increase in number. In addition to enhanced expression of pro-life genes, cancer cells down-regulate genes and their products that control pro-death signals, resulting in the accumulation and potential metastasis of life threatening cancer cells. Thus, combinations of unregulated cell proliferation and suppression of death inducing signaling pathways give cancer cells both growth and survival advantages.

Whether a cell increases in numbers or not depends on a balance of expression of negatively-acting and positively-acting growth regulatory gene products, and the presence or absence of functional cell death signaling pathways. Negative-acting growth regulatory genes contribute to blockage of cells in the cell cycle. Positive-acting growth regulatory genes stimulate cells to progress through the cell cycle. Genes involved in apoptosis can be either proapoptotic or antiapoptotic, and the dynamic balance between them determines whether a cell lives or dies. Cancer cells, in order to survive and increase their numbers, undergo a series of mutational events over time that remove regulatory controls that give them the ability to grow unchecked and survive even in the presence of proapoptotic signals, and develop attributes that permit them to escape detection and removal by the immune response defense system. Cancers may cause death of individuals unless removed by surgery or effectively treated with drugs.

A wide variety of pathological cell proliferative conditions exist for which novel therapeutic strategies and agents are needed to provide therapeutic benefits. These pathological conditions may occur in almost all cell types capable of abnormal cell proliferation or abnormal responsiveness to cell death signals. Among the cell types that exhibit pathological or abnormal growth and death characteristics are (1) fibroblasts, (2) vascular endothelial cells, and (3) epithelial cells. Thus, novel methods are needed to treat local or disseminated pathological conditions in all or almost all organ and tissue systems of individuals.

Most cancers, whether they are male specific, such as prostate or testicular, or female specific, such as breast, ovarian or cervical, or, whether they affect males and females equally, such as liver, skin or lung, with time undergo increased genetic lesions and epigenetic events, and eventually become highly metastatic and difficult to treat. Surgical removal of localized cancers has proven effective only when the cancer has not spread beyond the primary lesion. Once the cancer has spread to other tissues and organs, the surgical procedures must be supplemented with other more specific procedures to eradicate the diseased or malignant cells. Most of the commonly utilized supplementary procedures for treating diseased or malignant cells such as chemotherapy or bioradiation are not localized to the tumor cells and, although they have a proportionally greater destructive effect on malignant cells, often affect normal cells to some extent.

Some natural vitamin E compounds, and some derivatives of vitamin E have been used as proapoptotic and DNA synthesis inhibiting agents. Structurally, vitamin E is composed of a chromanol head and an alkyl side chain. There are eight major naturally occurring forms of vitamin E: alpha ($\alpha$), beta ($\beta$), gamma ($\gamma$), and delta ($\delta$) tocopherols and $\alpha$, $\beta$, $\gamma$, and $\delta$ tocotrienols. Tocopherols differ from tocotrienols in that they have a saturated phytyl side chain rather than an unsaturated isoprenyl side chain. The four forms of tocopherols and tocotrienols differ in the number of methyl groups on the chromanol head ($\alpha$ has three, $\beta$ and $\gamma$ have two and $\delta$ has one).

RRR-$\alpha$-tocopheryl succinate is a derivative of RRR-$\alpha$-tocopherol that has been structurally modified via an ester linkage to contain a succinyl moiety instead of a hydroxyl moiety at the 6-position of the chroman head. This ester linked succinate moiety of RRR-$\alpha$-tocopherol has been the most potent form of vitamin E affecting the biological actions of triggering apoptosis and inhibiting DNA synthesis. This form of vitamin E induces tumor cells to undergo apoptosis, while having no apoptotic inducing effects on normal cells. The succinated form of vitamin E is effective as an anticancer agent as an intact agent; however, cellular and tissue esterases that can cleave the succinate moiety, thereby converting the succinate form of RRR-$\alpha$-tocopherol to the free RRR-$\alpha$-tocopherol, render this compound ineffective as an anticancer agent. RRR-$\alpha$-tocopherol exhibits neither antiproliferative nor proapoptotic biological activity in cells of epithelial or immune origin. Attachment of the succinate moiety to the C-6 carbon on the chromonal ring of RRR-$\alpha$-tocopherol via an ether linkage provides stable tocopherol based apoptotic inducing compounds that can not be rendered ineffective since cells do not have etherases to clip off the succinate moiety.

To understand, in part, the mechanisms of action of tocopherols and tocotrienols as anticancer agents requires an understanding of their binding and their inter- and intra-cellular transport, via proteins that specifically interact with these compounds. It is well established that very low density lipoproteins (VLDLs) are loaded with RRR-$\alpha$-tocopherol in the liver (2) allowing for the entrance of RRR-$\alpha$-tocopherol into circulation. The liver protein alpha-tocopherol transport protein(-$\alpha$-TTP) has been shown to be involved in this process (3, 4). The sequence of $\alpha$-TTP has been reported and the protein exhibits specificity for the RRR-$\alpha$-tocopherol form, compared to the other isomers and forms of vitamin E (5–7). Another small molecular weight protein has been reported to be present in various tissues (8–10) however, the sequence or the role of this protein remains unidentified.

Recently, a protein was identified from humans and from bovine as having specificity for the RRR-forms of tocopherol (11, 12). The protein is 46 KDa in mass and has a characteristic CRAL-TRIO domain, a domain involved in binding to hydrophobic ligands (13). This protein was called tocopherol-associated protein (TAP-46). A more recent paper, however, identified the identical protein as having a role in enhancing cholesterol biosynthesis by promoting the conversion of squalene to lanosterol and called the protein supernatant protein factor (SPF) (14).

The prior art is an effective means of inhibiting undesirable or uncontrollable cell proliferation in a wide variety of pathophysiological conditions while having no to little effect on normal cells. The present invention fulfills this long-standing need and desire in the art.

SUMMARY OF THE INVENTION

This invention relates to the c-DNA cloning and nucleotide sequencing of a tocopherol associated protein (TAP-38), from human normal and breast cancer cells, and data showing TAP-38 as well as TAP-46 to have a role in the ability of novel tocopherol compounds to induce cancer cells to undergo growth arrest via inhibition of DNA synthesis, induction of cellular differentiation, and induction of apoptosis.

Whether TAP/SPF plays a role in the ability of vitamin E compounds to induce tumor cells to undergo cell death by apoptosis was examined. cDNA's from normal and breast cancer cells were cloned, and the presence of at least two tocopherol associated proteins, the previously reported tocopherol associated protein (TAP-46), and a novel tocopherol associated protein referred to herein as tocopherol associated protein-38 (TAP-38) were demonstrated.

TAP-38 cDNA differs from TAP-46 in that there is a 76 nucleotide deletion followed by 90 nucleotide mismatch sequences, and then an insertion of a single nucleotide. Thus, TAP-38 protein differs from TAP-46 protein by 55 amino acids (25 amino acid deletion and 30 novel amino acids). Evidence is provided that both TAP-38 and TAP-46 play a role in the ability of vitamin E compounds to inhibit tumor cell growth.

In one embodiment of the present invention, there is provided an isolated and purified DNA encoding tocopherol associated protein-p38 selected from the group consisting of: (a) isolated DNA which encodes said tocopherol associated protein-p38; (b) isolated c-DNA which hybridizes to isolated genomic DNA of (a) above and which encodes said tocopherol associated protein-p38; and (c) isolated DNA differing from the isolated DNAs of (a) and (b) above in codon sequence due to the degeneracy of the genetic code, and which encodes said tocopherol associated protein-p38.

In another embodiment of the present invention there is provided a Isolated and purified tocopherol associated protein-p38 coded for by DNA selected from the group consisting of: (a) isolated DNA which encodes said tocopherol associated protein-p38; (b) isolated DNA which hybridizes to isolated DNA of (a) above and which encodes said tocopherol associated protein-p38; and (c) isolated DNA differing from the isolated DNAs of (a) and (b) above in codon sequence due to the degeneracy of the genetic code, and which encodes said tocopherol associated protein-p38.

In yet another embodiment of the present invention there is provided a method for the treatment of cell proliferative diseases comprising the step of: administering to an animal a pharmacologically effective dose of a vector comprising the DNA encoding tocopherol associated protein-p38 or tocopherol associated protein-p46 selected from the group consisting of: (a) isolated DNA which encodes said tocopherol associated protein-p38 or tocopherol associated protein-p46; (b) isolated DNA which hybridizes to isolated DNA of (a) above and which encodes said tocopherol associated protein-p38 or tocopherol associated protein-p46; and (c) isolated DNA differing from the isolated DNAs of (a) and (b) above in codon sequence due to the degeneracy of the genetic code, and which encodes said tocopherol associated protein-p38 or tocopherol associated protein-p46 and regulatory elements necessary for expression of the DNA in a cell.

Other and further aspects, features, benefits, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention are briefly summarized. The above may be better understood by reference to certain embodiments thereof, which are illustrated in the appended drawings. These drawings form a part of the specification. It is to be noted; however, that the appended drawings illustrate preferred embodiments of the invention and therefore are not to be considered limiting in their scope.

FIG. 1 shows a cDNA sequence of TAP-38 (SEQ ID No. 1).

FIG. 2 shows a predicted amino acid sequence of TAP-38.

FIG. 3 shows a cDNA sequence comparison of TAP-38 (SEQ ID No. 1) and TAP-46 (SEQ ID No. 3).

FIG. 4 shows a predicted amino acid sequence comparison of TAP-38 (SEQ ID No. 2) and TAP-46 (SEQ ID No. 4) proteins.

FIGS. 13(A–B) show that tocopherol associated protein-46 (TAP-46) is important for tocopherol-based compounds (including α-TEA, VES, and δT3) to induce MDA-MB-435 human breast cancer cells to undergo cell death by apoptosis, and that TAP siRNA is an effective blocker of TAP-46 expression.

DETAILED DESCRIPTION OF THE INVENTION

Figure 5:
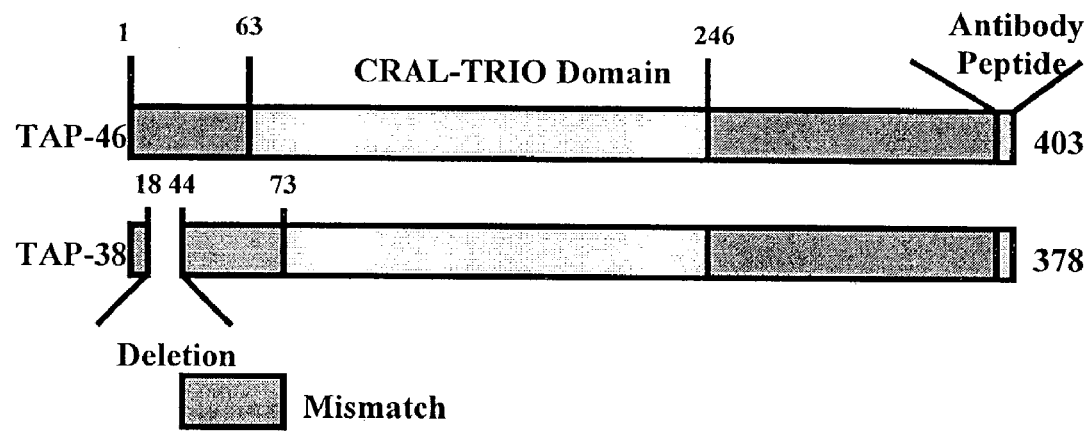
FIG. 5 shows a schematic illustrating the amino acid deletion and novel amino acids of TAP-38 proteins.

In one aspect, the present invention is directed to an isolated and purified DNA encoding tocopherol associated protein-p38 selected from the group consisting of: (a) isolated DNA which encodes said tocopherol associated protein-p38; (b) isolated DNA which hybridizes to isolated DNA of (a) above and which encodes said tocopherol associated protein-p38; and (c) isolated DNA differing from the isolated DNAs of (a) and (b) above in codon sequence due to the degeneracy of the genetic code, and which encodes said tocopherol associated protein-p38. A represenative example of such a DNA has the sequence shown in SEQ ID NO: 1 and encodes a protein having the predicted amino acid sequence shown in SEQ ID NO: 2.

In another aspect, the present invention is directed to a vector comprising the DNA of the present invention and regulatory elements necessary for expression of the DNA in a cell. An example of such a vector is one that contains DNA which encodes a tocopherol associated protein-p38 having the amino acid sequence shown in SEQ ID NO: 2. Preferably, the vector is a plasmid. One representative plasmid is a TAP-38 c-DNA plasmid containing a HA-tag. Expression of the mutant HA-tagged TAP-38 protein can sensitize tumor cells to induction of apoptosis by apoptotic inducing agents. Another representative plasmid is a TAP-38 c-DNA plasmid containing green fluorescent protein. Use of this plasmid permits one to determine if TAP-38 is regulated (translocated from cytosol to nucleus) by different forms of vitamin E. Another representative plasmid is a TAP-38 c-DNA plasmid containing a GST tag. This plasmid permits analyses of phosphorylation status of TAP-38 protein, and analyses of TAP-38 associated protein complexes. Another representative plasmid is a TAP-38 c-DNA plasmid containing a HIS tag. This plasmid permits the production and purification of high levels of TAP-38 protein to be used for amino acid sequence analyses, and for for vitamin E binding activity assays In another aspect, the present invention is directed to a TRE vector comprising a doxocycline inducible TAP-38. This vector is used to transfect and select cell lines stably expressing TAP-38. Such cells are used to examine the contributions of varying levels of TAP-38 protein to the anti-tumor properties of vitamin E compounds.

In another aspect, the present invention is directed to a host cell transfected with the vector of the present invention, the vector expresses the tocopherol associated protein-p38. The host cell cell may be a bacterial cell such as E. coli., a mammalian cell, a plant cells or an insect cell.

In another aspect, the present invention is directed to an isolated and purified tocopherol associated protein-p38 coded for by DNA selected from the group consisting of: (a) isolated DNA which encodes the tocopherol associated protein-p38; (b) isolated DNA which hybridizes to isolated DNA of (a) above and which encodes the tocopherol associated protein-p38; and (c) isolated DNA differing from the isolated DNAs of (a) and (b) above in codon sequence due to the degeneracy of the genetic code, and which encodes the tocopherol associated protein-p38. Preferably, the isolated and purified tocopherol associated protein-p38 has the amino acid sequence shown in SEQ ID NO: 2.

In yet another aspect, the present invention is directed to an antibody directed against the tocopherol associated protein-p38 of the present invention. Preferably, the antibody is a monoclonal antibody.

In yet another aspect, the present invention is directed to a mutated tocopherol associated protein-p38, wherein said protein has a mutation that enhances biological function, said mutation selected from the group consisting of a mutation to the ligand binding domain, a mutation to the transactivation domain, a mutation to the nuclear localization domain, a mutation to the sequence specific DNA binding domain, a mutation to the non-sequence specific DNA binding domain, a mutation to the dimerization or tetramerization domain, and a mutation to a phosphorylation and dephosphrylation site.

In still yet another aspect, the present invention is directed to a method for the treatment of cell proliferative diseases comprising the step of: administering to an animal a pharmacologically effective dose of a vector comprising the DNA encoding tocopherol associated protein-p38 or tocopherol associated protein-p46 selected from the group consisting of: (a) isolated DNA which encodes said tocopherol associated protein-p38 or tocopherol associated protein-p46; (b) isolated DNA which hybridizes to isolated DNA of (a) above and which encodes the tocopherol associated protein-p38 or tocopherol associated protein-p46; and (c) isolated DNA differing from the isolated DNAs of (a) and (b) above in codon sequence due to the degeneracy of the genetic code, and which encodes the tocopherol associated protein-p38 or tocopherol associated protein-p46 and regulatory elements necessary for expression of the DNA in a cell. Generally, the isolated and purified tocopherol associated protein-p38 or tocopherol associated protein-p46 is coded for by DNA selected from the group consisting of: (a) isolated DNA which encodes the tocopherol associated protein-p38 or tocopherol associated protein-p46; (b) isolated DNA which hybridizes to isolated DNA of (a) above and which encodes the tocopherol associated protein-p38 or tocopherol associated protein-p46; and (c) isolated DNA differing from the isolated DNAs of (a) and (b) above in codon sequence due to the degeneracy of the genetic code, and which encodes the tocopherol associated protein-p38 or tocopherol associated protein-p46. Preferably, the isolated and purified tocopherol associated protein-p38 has the amino acid sequence shown in SEQ ID NO: 2 and the tocopherol associated protein-p46 has the amino acid and nucleotide sequences shown in SEQ ID NOs: 3 and 4. This method can make use of a plasmid such as those described above and this method may be used to treat a human or non-human animal. Generally, this method may be used to treat a cell proliferative disease such as a neoplastic disease or a non-neoplastic disorder. Representative neoplastic diseases include ovarian cancer, cervical cancer, endometrial cancer, bladder cancer, lung cancer, breast cancer, testicular cancer, prostate cancer, gliomas, fibrosarcomas, retinoblastomas, melanomas, soft tissue sarcomas, ostersarcomas, leukemias, colon cancer, carcinoma of the kidney, pancreatic cancer, basal cell carcinoma and squamous cell carcinoma. Representative non-neoplastic proliferative diseases include psoriasis, benign proliferative skin diseases, ichthyosis, papilloma, restinosis, scleroderma, hemangioma, leukoplakia, viral diseases, autoimmune disorders and autoimmune diseases. Representative autoimmune diseases include autoimmune thyroiditis, multiple sclerosis, myasthenia gravis, systemic lupus erythematosus, dermatitis herpetiformis, celiac disease, and rheumatoid arthritis. A representative viral disorder is Human Immunodeficiency Virus infection. Representative autoimmune disorders include inflammatory processes involved in cardiovascular plaque formation, ultraviolet radiation induced skin damage, and disorders involving an immune component.

In a preferred embodiment of this method of the present invention, the vector is administered in the form of an aerosolized liposome. A representative liposome, but not limited to a single lipsome-inducing agent, is formulated with dilauroylphosphatidylcholine and the aerosol may comprise about 5% to 7.5% carbon dioxide. More particularly, the aerosol may have a ratio of polyethylenimine nitrogen to DNA phosphate (nitrogen:phosphate) is from about 5:1 to about 20:1. Generally, this method may be used to inhibit tumor cell growth by apoptosis, DNA synthesis arrest, cell cycle arrest, cellular differentiation or tumor cell metastases.

In a preferred embodiment of this method of the present invention, the method may further comprise the step of administering an anti-cancer compound before or after administering the vector. Representative anti-cancer drugs include 9-nitrocamptothecin, paclitaxel, doxorubicin, 5-fluorouracil, mitoxantrone, vincristine, cisplatin, epoposide, tocotecan, tamoxifen, and carboplatin. In one aspect, the anti-cancer drug is administered in the form of an aerosolized liposome. Optionally, the vector and said anti-cancer drug are administered concurrently in the form of an aerosolized liposome.

Treatment may be effected by administering a pharmacologically effective dose of the instant compounds of about 1 mg/kg to about 100 mg/kg. Administration of such a dose may be by oral, topical, liposomal/aerosol, intraocular, intranasal, parenteral, intravenous, intramuscular, or subcutaneous delivery.

The compounds and methods of the present invention may be used to treat non-neoplastic diseases that develop due to failure of selected cells to undergo normal programmed cell death or apoptosis. Representative examples of diseases and disorders that occur due to the failure of cells to die are autoimmune diseases. Autoimmune diseases are characterized by immune cell destruction of self cells, tissues and organs. A representative group of autoimmune diseases includes autoimmune thyroiditis, multiple sclerosis, myasthenia gravis, systemic lupus erythematosus, dermatitis herpetiformis, celiac disease, and rheumatoid arthritis. This invention is not limited to autoimmunity, but includes all disorders having an immune component, such as the inflammatory process involved in cardiovascular plaque formation, or ultra violet radiation induced skin damage.

The compounds and methods of the present invention may be used to treat disorders and diseases that develop due to viral infections. Representative examples of diseases and disorders that occur due to viral infections are human immunodeficiency viruses (HIV). Since these compounds are working on intracellular signaling networks, they have the capacity to impact signal transduction of any type of external cellular signal such as cytokines, viruses, bacteria, toxins, heavy metals, etc.

The following definitions are given for the purpose of facilitating understanding of the inventions disclosed herein. Any terms not specifically defined should be interpreted according to the common meaning of the term in the art.

As used herein, the terms "tocopherol associated protein-38 (TAP-38) c-DNA and protein" and tocopherol associated protein-46 (TAP-46) cDNA and protein" and "TAP-38 and TAP-46 antitumor functions" shall include the expression and analyses of TAP-38 and TAP-46 and constructs in vitro and in vivo.

As used herein, the term "individual" shall refer to animals and humans.

As used herein, the term "biologically inhibiting" or "inhibition" of the growth of proliferating cells shall include partial or total growth inhibition and also is meant to include decreases in the rate of proliferation or growth of the cells. The biologically inhibitory dose of the composition of the present invention may be determined by assessing the effects of the test element on target malignant or abnormally proliferating cell growth in tissue culture, tumor growth in animals and cell culture or any other method known to those of ordinary skill in the art.

As used herein, the term "induction of programmed cell death or apoptosis" shall include partial or total cell death with cells exhibiting established morphological and biochemical apoptotic characteristics. The dose of the composition of the present invention that induces apoptosis may be determined by assessing the effects of the test element on target malignant or abnormally proliferating cell growth in tissue culture, tumor growth in animals and cell culture or any other method known to those of ordinary skill in the art.

As used herein, the term "induction of cell cycle arrest" shall include growth arrest due to treated cells being blocked in GO/G1 or G2/M cell cycle phase. The dose of the composition of the present invention that induces cell cycle arrest may be determined by assessing the effects of the test element on target malignant or abnormally proliferating cell growth in tissue culture, tumor growth in animals and cell culture or any other method known to those of ordinary skill in the art.

As used herein, the term "induction of cellular differentiation" shall include growth arrest due to treated cells being induced to undergo cellular differentiation as defined by established morphological and biochemical differentiation characterization, a stage in which cellular proliferation does not occur. The dose of the composition of the present invention that induces cellular differentiation may be determined by assessing the effects of the test element on target malignant or abnormally proliferating cell growth in tissue culture, tumor growth in animals and cell culture or any other method known to those of ordinary skill in the art.

As used herein, the term "growth inhibitory concentration ($IC_{50}$)" or "effective concentration ($EC_{50}$)" shall include the effective therapeutic dose of a compound or composition for controlling cancer growth, i.e., by blocking 50% cancer growth via DNA synthesis inhibition, cellular differentiation, cell cycle blockage and/or cell death.

The pharmacodynamically designed compounds of the present invention have an improved therapeutic index and are potent inhibitors of cancer cell growth; i.e., they demonstrate high antitumor activity with minimal side effects. These compounds, which can not be readily degraded since there are no known etherases in mammals, may be used in the treatment of cancers and disorders involving excess cell proliferation, as well as for cells that accumulate in numbers due to suppressed cell killing mechanisms, with minimal side effects. The compounds of the present invention inhibit cancer cell growth by induction of cell differentiation, induction of apoptosis and DNA synthesis arrest. Induction of apoptosis and, by extension, inhibition of tumor growth, by these compounds is via modulation of the transforming growth factor-beta (TGF-β), Fas/Fas ligand, and certain mitogen-activated protein kinases (MAPK) signaling pathways, or, in the case of some tocotrienols, is expected to involve these pathways. Induction of apoptosis via other pathways, such as ceramide production, is not excluded. These growth inhibitory properties allow these compounds to be used in the treatment of proliferative diseases, including cancers of different cell types and lineages, non-neoplastic hyperproliferative diseases, and disorders with defects in apoptotic signaling pathways. Several of the compounds of the present invention are both strong inducers of apoptosis and strong inhibitors of DNA synthesis arrest of tumor cells representing different cellular lineages.

As used herein, the term "inhibition of metastases" shall include partial or total inhibition of tumor cell migration from the primary site to other organs. The biological level of the composition of the present invention that enhances inhibition of metastasis by tocopherol based compounds may be determined by assessing the effects of the test element on target malignant or abnormally proliferating cell growth in tissue culture, tumor growth in animals and cell culture or any other method known to those of ordinary skill in the art.

As used herein, the term "inhibition of angiogenesis" shall include partial or total inhibition of tumor blood vessel formation or reduction in blood carrying capacity of blood vessels supplying blood to tumors.

As used herein, the term "induction of programmed cell death or apoptosis" shall include partial or total cell death with cells exhibiting established morphological and biochemical apoptotic characteristics. The biological level of the composition of the present invention that enhances the induction of apoptosis by tocopherol based compounds may be determined by assessing the effects of the test element on target malignant or abnormally proliferating cell growth in tissue culture, tumor growth in animals and cell culture or any other method known to those of ordinary skill in the art.

As used herein, the term "induction of DNA Synthesis Arrest" shall include growth arrest due to treated cells being blocked in GO/G1, S, or G2/M cell cycle phases. The dose of the composition of the present invention that enhances the induction of DNA synthesis arrest by tocopherol based compounds may be determined by assessing the effects of the test element on target malignant or abnormally proliferating cell growth in tissue culture, tumor growth in animals and cell culture or any other method known to those of ordinary skill in the art.

As used herein, the term "induction of Cellular Differentiation" shall include growth arrest due to treated cells being induced to undergo cellular differentiation as defined by established morphological and biochemical differentiation characterization, a stage in which cellular proliferation does not occur. The dose of the composition of the present invention that enhances the induction of cellular differentiation by tocopherol based compounds may be determined by assessing the effects of the test element on target malignant or abnormally proliferating cell growth in tissue culture, tumor growth in animals and cell culture or any other method known to those of ordinary skill in the art.

Stable and transient transfections, infections, and aerosol liposome method for delivery of TAP-38 or TAP-46, separately or in combination with other anticancer agents, of the present invention may be used to treat neoplastic diseases and non-neoplastic diseases. Representative examples of neoplastic diseases are ovarian cancer, cervical cancer, endometrial cancer, bladder cancer, lung cancer, cervical cancer, breast cancer, prostate cancer, testicular cancer, gliomas, fibrosarcomas, retinoblastomas, melanomas, soft tissue sarcomas, osteosarcomas, colon cancer, carcinoma of the kidney, pancreatic cancer, basal cell carcinoma, and squamous cell carcinoma. Representative examples of non-neoplastic diseases are selected from the group consisting of psoriasis, benign proliferative skin diseases, ichthyosis, papilloma, restinosis, scleroderma and hemangioma, and leukoplakia.

Methods of the present invention may be used to treat non-neoplastic diseases that develop due to failure of selected cells to undergo normal programmed cell death or apoptosis. Representative examples of diseases and disorders that occur due to the failure of cells to die are autoimmune diseases. Autoimmune diseases are characterized by immune cell destruction of self cells, tissues and organs. A representative group of autoimmune diseases includes autoimmune thyroiditis, multiple sclerosis, myasthenia gravis, systemic lupus erythematosus, dermatitis herpetiformis, celiac disease, and rheumatoid arthritis. This invention is not limited to autoimmunity, but includes all disorders having an immune component, such as the inflammatory process involved in cardiovascular plaque formation, or ultra violet radiation induced skin damage.

Methods of the present invention may be used to treat disorders and diseases that develop due to viral infections. Representative examples of diseases and disorders that occur due to viral infections are human immunodeficiency viruses (HIV). Since the expression of TAP-38 or TAP-46 by tumor cells will likely render the cells more responsive to tocopherol based apoptotic inducing agents, this invention has the capacity to impact signal transduction of any type of external cellular signal such as cytokines, viruses, bacteria, toxins, heavy metals, etc.

The methods of the present invention may be used to treat any animal. Most preferably, the methods of the present invention are useful in humans.

Generally, to achieve pharmacologically efficacious cell killing and anti-proliferative effects, these compounds and analogs thereof may be administered in any therapeutically effective dose. Preferably, the structurally modified tocopherols and tocotrienols and analogs are administered in a dose of from about 0.1 mg/kg to about 100 mg/kg. More preferably, the structurally modified tocopherols and tocotrienols and analogs are administered in a dose of from about 1 mg/kg to about 10 mg/kg.

Administration of the compounds and compositions of the present invention may be by liposome/aerosol, topical, intraocular, parenteral, oral, intranasal, intravenous, intramuscular, subcutaneous, or any other suitable means. The dosage administered is dependent upon the age, clinical stage and extent of the disease or genetic predisposition of the individual, location, weight, kind of concurrent treatment, if any, and nature of the pathological or malignant condition. The effective delivery system useful in the method of the present invention may be employed in such forms as liposomal aerosol, capsules, tablets, liquid solutions, suspensions, or elixirs, for oral administration, or sterile liquid forms such as solutions, suspensions or emulsions. For topical use it may be employed in such forms as ointments, creams or sprays. Any inert carrier is preferably used in combination with suitable solubilizing agents, such as saline, or phosphate-buffered saline, or any such carrier in which the compounds used in the method, such as ethanol, acetone, or DMSO, of the present invention have suitable solubility properties.

There are a wide variety of pathological cancerous and noncancerous cell proliferative conditions and cell accumulations due to absence of normal cellular death for which the compositions and methods of the present invention will provide therapeutic benefits. These pathological conditions may occur in almost all cell types capable of abnormal cell proliferation or defective in programmed cell death mechanisms. Among the cell types which exhibit pathological or abnormal growth or abnormal death are (1) fibroblasts, (2) vascular endothelial cells and (3) epithelial cells. It can be seen from the above that the methods of the present invention is useful in treating local or disseminated pathological conditions in all or almost all organ and tissue systems of individuals.

Thus the present invention is directed toward the design and effective use of novel agents that can specifically target cancer cells and either down-regulate growth stimulatory signals, up-regulate growth inhibitory signals, down-regulate survival signals and/or up-regulate death signals. More specifically, this invention creates and characterizes novel agents that activate growth inhibitory factors, trigger death signaling pathways, and inhibit DNA synthesis.

The following examples are given for the purpose of illustrating various embodiments of the invention and are not meant to limit the present invention in any fashion.

EXAMPLE 1

Cloning Procedures

The coding area of the cDNA for human TAP was amplified by RT-PCR using total RNA from MDA-MB-435 and MCF-7 human breast cancer cell lines. The total RNA was extracted using RNeasy Mini Kit (Cat# 74104, Qiagen) following company instructions. The TAP oligonucleotide primers were synthesized based on the published TAP sequence (Accession # $NM_{13}012429$) with sense oligomer primer (5'-ATG AGC GGC AGA GTC GGC GAT-3') (SEQ ID NO: 5) and antisense oligomer primer (5'-TTA TTT CGG GGT GCC TGC CCC CA-3') (Integrated,DNA Technologies, Inc IDT) (SEQ ID NO: 6). RT-PCR condition; 5 µg total RNA was used with random primer (Cat# 48190–011 lot# 1088038 GIBCOBRL). The denaturation at 65° C. for 5 minutes, reverse transcription at 42° C. for 50° C. min and inactivation at 70° C. for 15 minutes PCR conditions; 5 µl of RT-PCR product was used for PCR with 40 cycles; 94° C. for 30 s, 70° C. for 1 minute and 72° C. for 1 minute.

Figure 6:
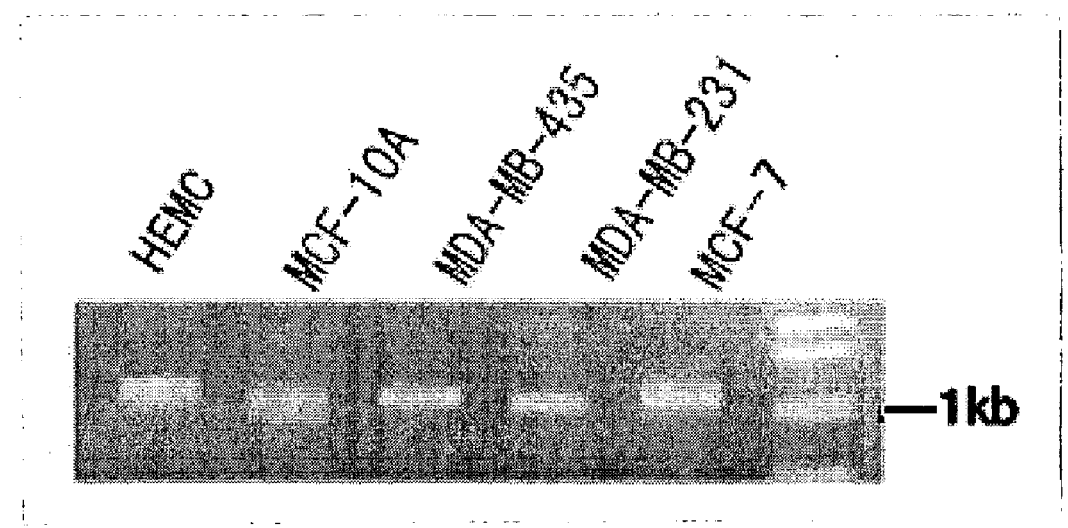
FIG. 6 shows PCR products of TAP isolated from different breast cancer cell lines. (HEMC=human epithelial mammary cells; M10A=immortalized but non-tumorigenic human mammary cells; MDA-MB-435=estrogen non-responsive human breast cancer cells; MDA-MB-231=estrogen non-responsive human breast cancer cells; and MCF-7=estrogen responsive human beast cancer cells).

The about 1.2 kD PCR product (FIG. 6) was purified with QIAquick Gel Extraction Kit (Cat# 28704, Qiagen) and subcloned into the pGEM-T vector (Cat# A3610, Promega) after an A-tailing procedure following the company instructions (promega). The construct was transformed into JM109 competent cells (Cat# A3610, Promega) using heat shock. Clones were sequenced using M13 forward and reverse oligomer primers (Integrated DNA Technologies, Inc IDT).

EXAMPLE 2 c-DNA Sequence Comparison of TAP-38 with TAP-46 (FIGS. 1 & 3).

FIG. 1 shows a c-DNA sequence comparison of TAP-38 with TAP-46. TAP-38 cDNA has a deletion starting at base nucleotide 55 and continuing to base nucleotide 131 resulting in a 76 base nucleotide deletion. Thus, the first 18 amino acids (nucleotides 1–54) code for 18 N-terminal tocopherol associated protein amino acids. There is a deletion of 25 amino acids and a disruption of the tocopherol associated protein triplets following codon 131 and extending to nucleotide position 222. There is a single base nucleotide insertion at position 223. Thus, base nucleotides 132 to 222 (90 base nucleotides) code for novel TAP-38 amino acids (30 amino acids).

TAP-38 nucleotides 224 to 1,137 exhibit 100% homology to TAP-46 nucleotides. Consequently, TAP-38 protein is 25 amino acids shorter than TAP-46 (403 minus 25=378 amino acids), and further differs from TAP-46 by 30 additional amino acids. The 25 amino acid deletion occurs in the N-terminal domain of tocopherol associated protein, a region the function of which remains to be determined. TAP-38's novel 30 amino acids extends into the CRAL-TRIO domain of tocopherol associated protein by 10 amino acids (this domain, as well as other regions has homology to TTP; retinal binding protein, SEC 14, PTN 9, and rat secretory protein 45 (FIGS. 2 & 4) (1).

FIG. 5 is a schematic diagram of TAP-38 protein showing the position of the 25 amino acid deletion (19–43) and the 30 novel amino acids (44–73) in relation to TAP-46. With the exception of the 25 amino acid deletion and the 30 novel amino acids, Tap-38 exhibits 100% homology to other regions of TAP-46.

EXAMPLE 3

Cloning of HA-Tagged TAP-38 and HA-Tagged TAP-46

For protein expression of 46 kDa and 38 kDa tocopherol associated protein a construct containing a HA-tag on the N-terminal site was designed. The sense primer for the PCR encoded an EcoRI restrict enzyme cutting site, starting codon and HA residue, and tocopherol associated protein sequence from 4–21 bases (5'-CGC GAA TTC ATG TAT GAT GTT CCT GAT TAT GCT AGC CTC AGC GGC AGA GTC GGC GAT) (SEQ ID NO: 7), and the antisense primer contained a stop codon of tocopherol associated protein and BamHI restriction enzyme cutting site. The RT-PCR and PCR conditions were the same as described above. The PCR products from MCF-7 and MDA-MB-435 cells were cloned into pGEM vectors. Three clones from each cell lines were sequenced using M13 forward and reverse oligomer primers (Integrated DNA Technologies, Inc IDT) described as above.

Figure 7:
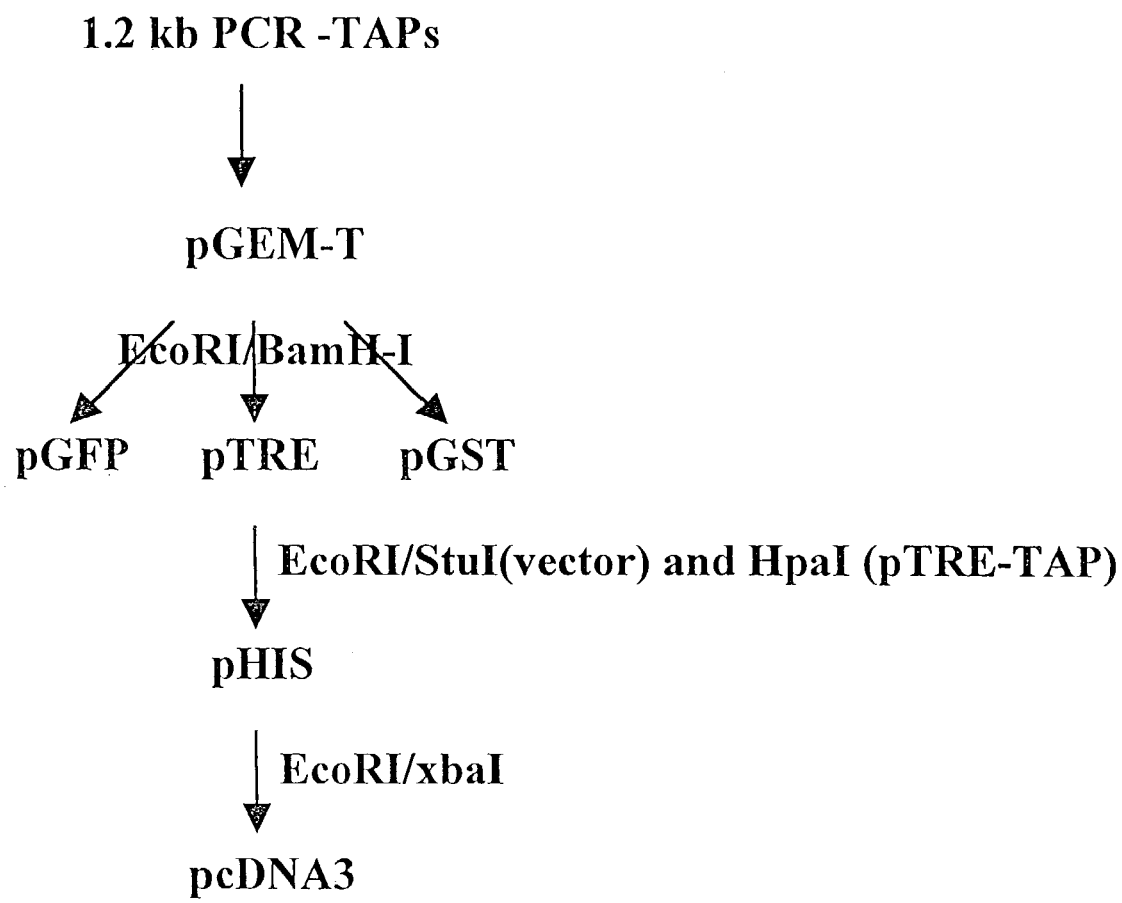
FIG. 7 shows a schematic illustrating the process for generating pGFP, pTRE, pGST, pHIS, and pcDNA3 plasmids.

To generate different plasmids, the 1.2 kb PCR-TAP product was subcloned into the pGEM-T vector. Next, EcoRI and BamH-1 endnucleases were used to generate plasmids containing pGFP, pTRE, and pGST. The pTRE construct was used to generate plasmids containing pHIS (using endonucleases EcoRI/StuI (vector) and HpaI (pTRE-TAP), and plasmid containing pcDNA3 (using EcoRI/xbal endonucleases) (FIG. 7).

EXAMPLE 4

Expression of HA-Tagged TAP-38 and HA-Tagged TAP-46 in MCF-7 and MDA-MB-435 Human Breast Cancer Cells MCF-7 and MDA-MB-435 cells were stably transfected with pTRE-HA-TAP-38 and TAP-46 vectors. Positive clones (three each) expressing TAP-38 and TAP-46 were selected by screening, using western blot with HA-tag antibody. MCF-7 and MDA-MB-435 cells were transiently transfected with pcDNA-3 HA-TAP-38 and HA-TAP-46 vectors.

EXAMPLE 5

Figure 8:
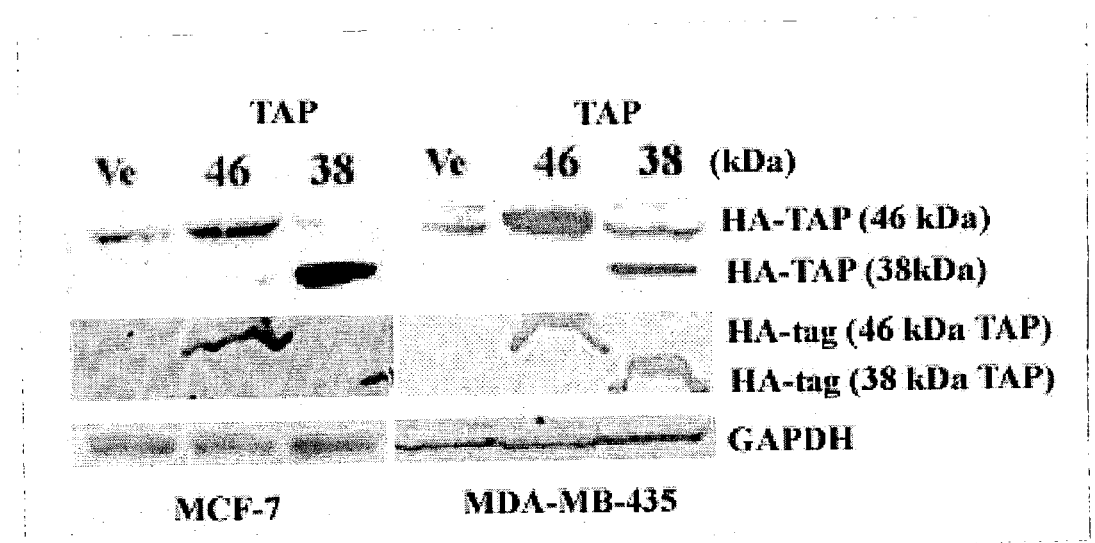
FIG. 8 shows the expression of HA-tagged TAP-38 protein and HA-tagged TAP-46 proteins in MCF-7 and MDA-MB-435 human breast cancer cells.

Functional Expression of HA-Tagged TAP-38 and HA-Tagged TAP-46 in MCF-7 and MDA-MB-435 Cells TAP-38 and TAP-46 proteins from cellular extracts was subjected to western blot analyses, using antibodies to HA-tag and antibodies to TAP c-terminus peptide (FIG. 8).

EXAMPLE 6

Transient Transfection of MDA-MB-435 Human Breast Cancer Cells with either TAP-38 or TAP-46

Figure 9:
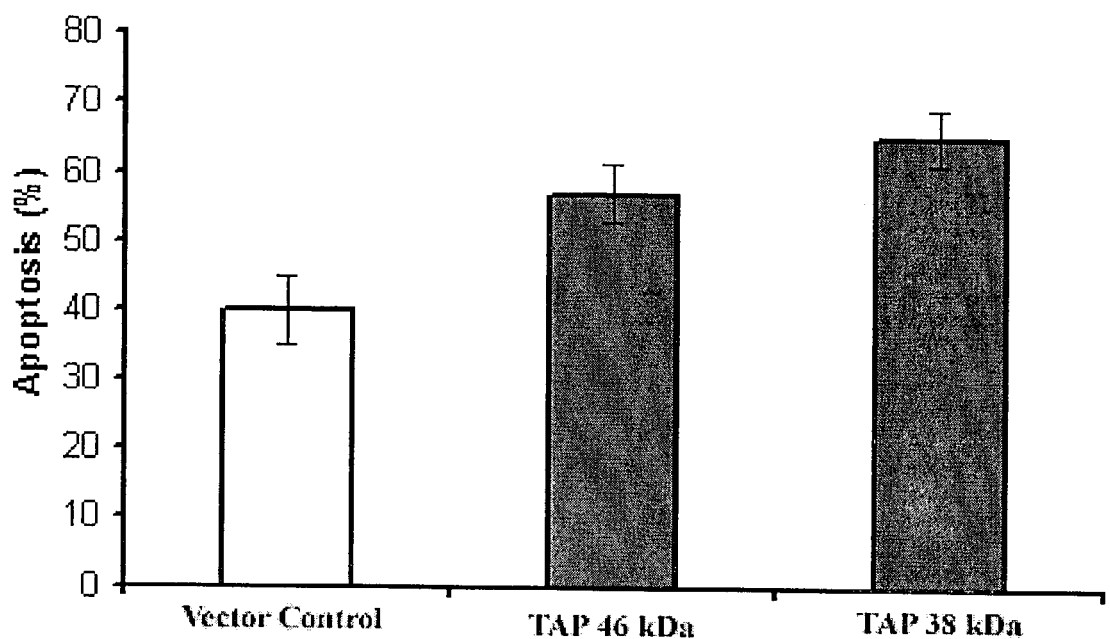
FIG. 9 shows enhanced apoptosis [above levels obtained with cells transiently transfected with vector only (vector control)] of human MDA-MB-435 breast cancer cells transiently transfected with TAP-38 and TAP-46 cDNA, followed by treatment with 20 micrograms/ml of compound #1 (Co#-1).

Transient transfection of MDA-MB-435 human breast cancer cells with either TAP-38 or TAP-46 enhanced the ability of tocopherol compound #1 [2,5,7,8-tetramethyl-(2R-(4R,8R,12-trimethyltridecycl) chroman-6-yloxy) acetic acid] to induce apoptosis (FIG. 9).

EXAMPLE 7

Figure 10:
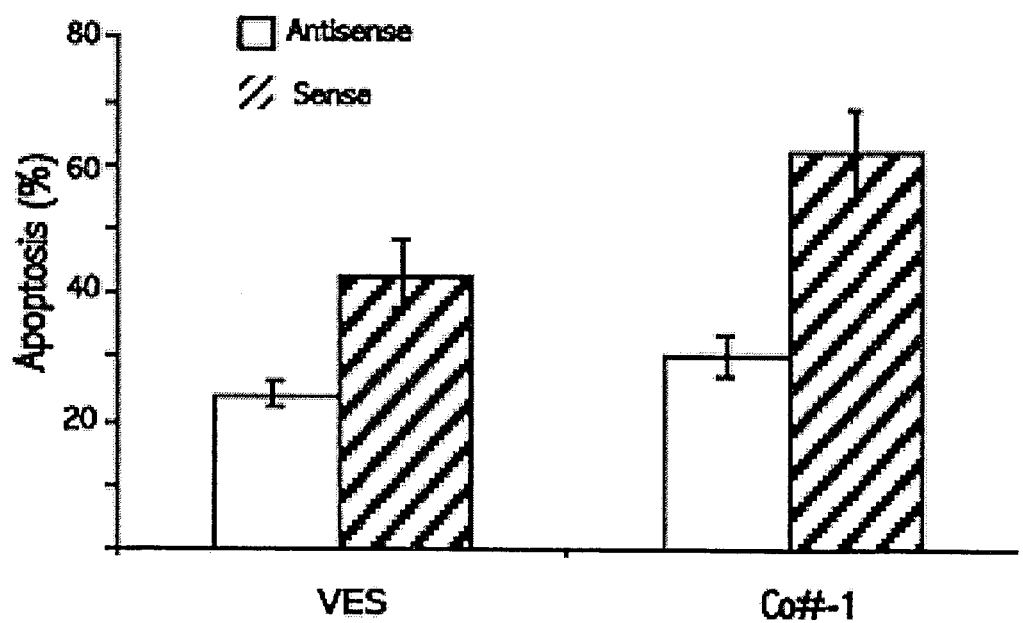
FIG. 10 shows that antisense oligomers to TAP (both TAP-38 and TAP-46) transiently transfected into human MDA-MB-435 cells block (in comparison to sense oligomer transfected cells) the ability of vitamin E succinate (VES) and compound #1 (Co#-1) to induce human MDA-MB-435 cells to undergo apoptosis. Apoptosis was determined by examination of nuclear condensation and fragmentation.

Transient Transfection of MDA-MB-435 Cells with Antisense Oligomers to the N-terminal Region of TAP Transient transfection of MDA-MB-435 cells with antisense oligomers to the N-terminal region of TAP (interferes with TAP-38 as well as TAP-46 transcription) blocked the ability of tocopherol compounds, vitamin E succinate and compound #1, to induce apoptosis, showing that TAP-38 and TAP-46 are involved in the ability of vitamin E compounds to inhibit tumor cell growth (FIG. 10).

EXAMPLE 8

Cloning of TAP-38 and TAP-46 Fused to Green Fluorescent Protein (GFP)

Figure 11:
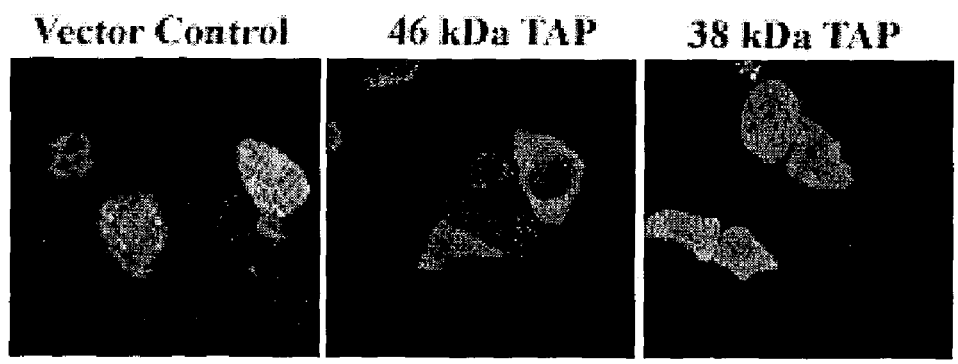
FIG. 11 shows the expression of green fluorescent protein (GFP) in the cytosol of human MDA-MB-435 cells transiently transfected with pGFP vector (control), transfected with GFP-TAP-38 cDNA, and transfected with GFP-TAP-46 cDNA.

Whether or not GFP-TAP localizes to specific cellular regions or organelles following treatment with tocopherol based compounds is examined (FIG. 11).

EXAMPLE 9

Antisense Oligomers to TAP

Figure 12:
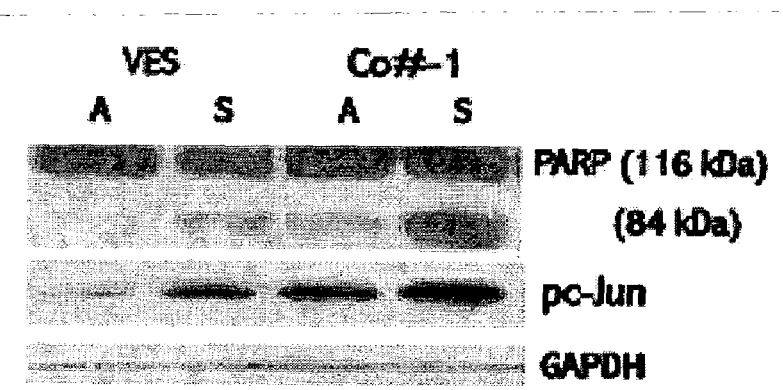
FIG. 12 shows that MDA-MB-435 cells transiently transfected with antisense (A) oligomers to TAP (both TAP-38 and TAP-46) [in comparison to sense oligomers (S)] exhibit reduced levels of apoptosis (as measured by PARP cleavage—PARP 116 kDA=intact protein and PARP-84 kDA=cleavage product) when treated with apoptotic inducing agents vitamin E succinate (VES) and compound #1 (Co#-1). Furthermore, antisense oligomers to TAP inhibited the phosphorylation of transcription factor protein c-Jun (pc-Jun) when MDA-MB-435 cells (transfected with antisense or sense oligomers) were treated with vitamin E succinate (VES) and compound #1 (Co#-1).

Antisense oligomers to TAP (both TAP-38 and TAP-46), showing that the induction of apoptosis with vitamin E succinate or compound #1 [2,5,7,8-tetramethyl-(2R-(4R,8R,12-trimethyltridecycl) chroman-6-yloxy) acetic acid] to involve tocopherol associated protein. Antisense oligomers to tocopherol associated protein, in comparison to sense oligomers to tocopherol associated protein, blocked the cleavage of poly ADP-ribose polymerase (PARP) when cells were treated with vitamin E succinate (VES) and compound #1 (Co#-1) [2,5,7,8-tetramethyl-(2R-(4R,8R,12-trimethyl-tridecycl) chroman-6-yloxy) acetic acid]. Furthermore, data show that antisense oligomers to tocopherol associated protein block the phosphorylation of c-Jun (FIG. 12).

EXAMPLE 10

Aerosol Liposome Plasmid DNA of TAP-38 or TAP-46 Preparation in Combination with other Apoptotic Inducing Agents The liposome formulation of TAP-38 or TAP-46 plus tocopherol based apoptotic inducing agents separately and in combination with other apoptotic inducing agents such as 9-nitro-camptothecin, doxorubicin, and taxol), will utilize polyethyleneimine following liposome/plasmid DNA procedures outlined in reference (6).

EXAMPLE 11

Aerosol Liposome/TAP-38 or TAP-46 Administration

Administration of TAP-38 or TAP-46 cDNA plasmid can be by infection, transfection, or by aerosol/liposomal preparation. The aerosol method of delivery of TAP-38 or TAP-46 CDNA plasmids will be given here as an example of a method of delivery. Aerosol liposome/TAP38 or TAP-46 plasmid DNA preparation, in combination with tocopherol based apoptotic inducing agents (or in combination with other chemotherapeutic agents) can be administered to any animal, including humans.

A method of aerosol delivery is illustrated using mice as a test animal. The liposome/TAP38 or TAP-46 plasmid DNA preparation and tocopherol based apoptotic inducing compounds (with and without other chemotherapeutic agents) is administered to tumor bearing and non-tumor bearing Balb/c mice in a sealed plastic cage. An air compressor (EZ-Air PM 15F, Precision Medical) producing a 10 L/min airflow is used with an Aero Mist nebulizer (CIS-US, Inc. Bedford, Mass.) to generate aerosol particles. The preparations are reconstituted by bringing the liposomes to room temperature then adding enough distilled water to bring the final volume to 5 mls. The solution is allowed to swell at room temperature for 30 minutes with periodic inversion and then added to the nebulizer. The nebulizer is connected via accordian tubing (1 cm inside diameter) to an entry in one end of the cage. Aerosol is discharged through an opening at the opposite end of the cage. For safety, nebulizing is done in a hood. Aerosol is administered to the mice in a closed container cage until all treatment is gone (approximately 30 minutes for delivery of total volume of 5 mls).

EXAMPLE 12

In Vivo Potential for Human Cancer Cells

The compositions of the present invention may be used as therapeutic agents. In vivo studies of tumor growth and metastasis of human tumor cells either ectopically or orthotopically transplanted into immune compromised animals, such as nude mice, or in vivo studies employing well recognized animal models are conducted. Inhibition of growth of human tumor cells transplanted into immune compromised mice provide pre-clinical data for clinical trials. In vivo studies are performed on the metastatic potential of non-estrogen responsive MDA-MB-435 human breast cancer model, and a murine syngenic 66cl.4-GFP mammary cancer model.

EXAMPLE 13

MDA-MB-435 Breast Cancer Model

Pathogen free MDA-MB-435 human breast cancer cells stably transfected with a marker protein (green fluorescence protein, GFP) are grown as a solid tumor in immune compromised nude mice. $1 \times 10^6$ tumor cells are orthotopically injected into the mammary fat pad or ectopically injected near the 4th and 5th nipples of female nude mice. When tumors reach a size of 1 mm, daily treatments with TAP-38 or TAP-46+tocophrol based compounds exhibiting apoptotic inducing properties are initiated. Tumor growth, metastasis, and death of treated and control animals are determined. Tumor growth is measured by caliper evaluations of tumor size. At the time of sacrifice, tumors are removed, measured for volume, and used for histochemical examination. Organs such as spleen, lymph nodes, lungs, and bone marrow, are examined for metastatic cells by histochemical staining of tissue sections for expression of the marker green fluorescence protein.

EXAMPLE 14

Murine Syngeneic 66cl.4-GFP Mammary Cancer Model

Pathogen free 66cl.4-GFP mammary cancer cells of Balb/c origin (100,000 to 200,000) are injected near the 4th and 5th nipples of female Balb/c mice. Treatments are as described above. Tumor metastases to lungs occur in 100% of the mice. Tumor growth, metastasis, and death of the animals are determined. Tumor growth is measured by caliper evaluations of tumor size. At the time of sacrifice, tumors are removed, measured for volume, and used for histochemical examination. Organs such as spleen, lymph nodes, lungs, and bone marrow, are examined for metastatic cells by histochemical staining of tissue sections for expression of the marker green fluorescence protein.

EXAMPLE 15

TAP-46 Blocking Experiments Using siRNA

MDA-MD-435 cells at $13.5 \times 10^6/55$ cm$^2$ cell culture dish (100 mm×20 mm; catalog # 430293, Corning Inc., Corning, N.Y.) were transiently transfected with in vitro transcribed TAP siRNA (Silencer siRNA Construction Kit, Ambion) using siPORT Lipid following company instructions (catalog # 4505, Ambion, Austin, Tex.). Cells were incubated overnight in culture media, then washed two times with non-supplemented regular MEM media. Next, the cells were incubated overnight in the presence of siRNA/siPORT Lipid [10 mM/16 µl or 16 µl siPORT lipid only (as control)] in 5 ml of serum free media (OPTI-MEMI, catalog # 31985–070, Gibco). SiRNA/siPORT Lipid complex was generated by two steps: 1) 16 µl of siPORT lipid was incubated with 60 µl of OPTI-MEMI media for 30 minutes at room temperature; and 2) 60 µl of siPORT Lipid in OPTI-MEMI was then incubated for 20 minutes with 500 µl of diluted TAP siRNA [or 500 µl media as control (5 µl of 10 µl TAP siRNA in 500 µl of of OPTI-MEMI media)]. The transfected cells were then split into 12 wells at $1.5 \times 10^5$ cells/well for apoptosis and 55 cm$^2$ dish at $3.5 \times 10^6$ cells/dish for Western immunoblot analyses.

Figure 13A:
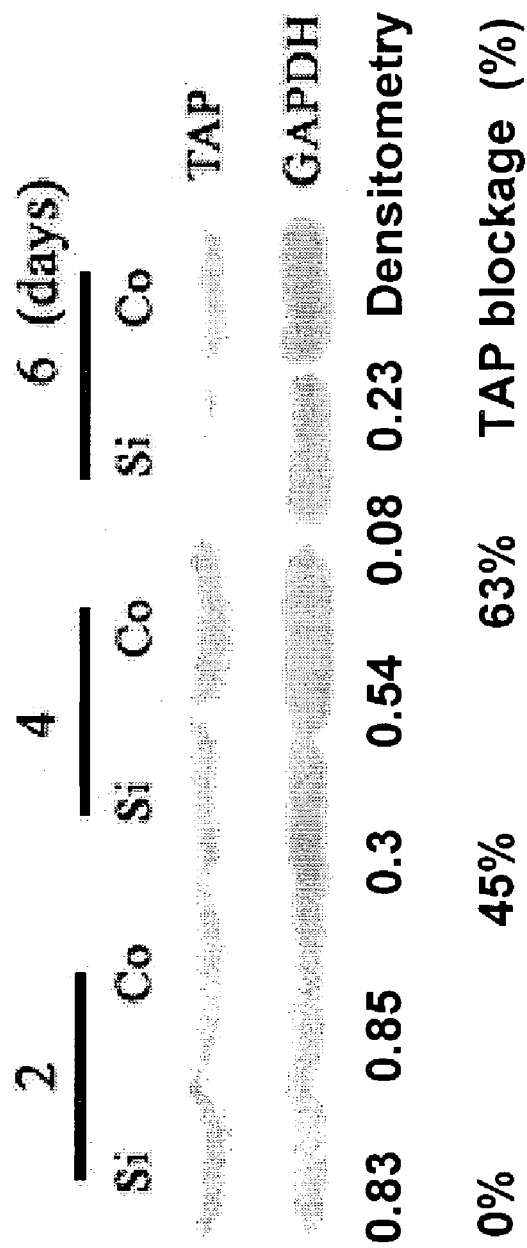
FIG. 13A shows that levels of TAP protein in cell lysates of human MDA-MB-435 breast cancer cells transiently transfected with small-interfering RNA (siRNA) targeted to TAP blocked the expression of TAP protein in a time-dependent manner. Si=cells transfected with TAP siRNA; Co=SiPORT lipid control levels; TAP=TAP-46; GAPDH levels were used as lane controls and for determining relative densitometric analyses.

The cells in 55 cm$^2$ dishes were incubated for 8 hours with culture media followed by treatment with 20 µg/ml of α-TEA in 2% serum treatment media for 15 hours. Cells were collected and fractionated, and the lysates were analyzed for TAP protein levels by Western immunoblotting (FIG. 13A). The cells plated in 12-well plates were incubated overnight in culture media followed by treatment with 20 µg/ml of α-TEA, 20 µg/ml of VES, and 5 µg/ml of RRR-δ-tocotrienol (dt3) and cultured for 2 days. Apoptosis was evaluated by DAPI staining (FIG. 13B).

The results shown in FIGS. 13(A–B) demonstrate that tocopherol-associated protein-46 (TAP-46) is important for tocopherol-based compounds (including α-TEA, VES, and δT3) to induce MDA-MB-435 human breast cancer cells to undergo cell death by apoptosis.

FIG. 13A shows that MDA-MB-435 cells transfected with TAP siRNA show reduced levels of cellular TAP-46. Levels of TAP protein in cell lysates of human MDA-435 breast cancer cells transiently transfected with small-interfering RNA (siRNA) targeted to TAP blocked the expression of TAP protein in a time-dependent manner. Transient transfection of TAP siRNA into MDA-MB-435 cellws for 2, 4, and 6 days inhibited the expression of TAP protein by 0%, 45%, and 63%, respectively. These data show that siRNA is an effective blocker for TAP-46 expression.

Figure 13B:
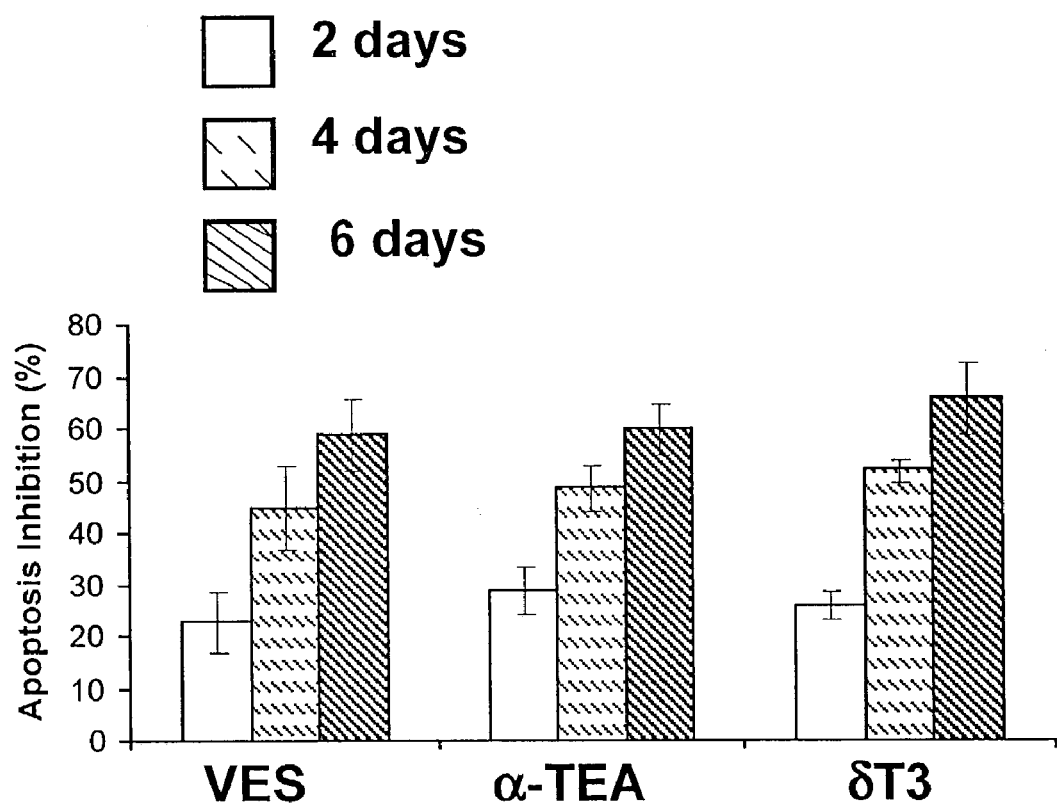
FIG. 13B shows that human MDA-MB-435 breast cancer cells transiently transfected with small-interfering TAP RNA (siRNA) for 2, 4, and 6 days, and then cultured for two days in the presence of VES, α-TEA or δT3 are inhibited from undergoing apoptosis.

FIG. 13B shows that MDA-MB-435 breast cancer cells transiently transfected with TAP siRNA for 2, 4, and 6 days, and then cultured for two days in the presence of VES, α-TEA or δT3 are inhibited from undergoing apoptosis. For example, cells transiently transfected with TAP siRNA for 6 days and then treated with α-TEA, VES, or δT3 were inhibited from induction of apoptosis by approximately 60% in comparison to control cells cultured with the three compounds for two days.

The following references are cited herein.

1. Zimmer S, Stocker A, Sarbolouki M N, Spycher S E, Sassoon J, Azzi A. A 1. novel human tocopherol-associated protein: cloning, in vitro expression, and characterization. Journal of Biological Chemistry 275; 25672–80, 2000.

2. Traber, M. G. and Arai, H. Molecular mechanisms of vitamin E transport. Annual Rev. Nutr., 19: 343–355, 1999.

3. Traber, M. G. and Sies, H. Vitamin E in humans: Demand and delivery. Annual Rev. Nutr. 16: 321–347, 1996.

4. Arita, M., Nomura, K., Arai, H., and Inoue, K. Alpha-tocopherol transfer protein stimulates the secretion of alpha-tocopherol from a cultured liver cell line through a brefeldin A-insensitive pathway. Proc. Natl. Acad. Sci. USA, 94: 12437–12441, 1997.

5. Ouahchi, K., Arita, M., Kayden, H., Hentati, F., Ben Hamida, M. Sokol, R., Arai, H., Inoue, K., Mandel, J. L., and Koenig, M. Ataxia with isolated vitamin E deficiency is caused by mutations in the alpha-tocopherol transfer protein. Nat. Genetics 9: 141–145, 1995.

6. Arita, M., Sato, Y., Miyata, A., Tanabe, T., Takashashi, E., Kayden, H. J., Arai, H., and Inoue, K. Human alha-tocopherol transfer protein: cDNA cloning, expression and chromosomal localization. Biochem J. 306: 437–443, 1995.

7. Hosomi, A., Arita, M., Sato, Y., Kiyose, C., Ueda, T., Igarashi, O., Arai, H., and Inoue, K. Affinity for alpha-tocopherol transfer protein as a determinant of the biological activities of vitamin E analogs. FEBS Lett, 409: 105–108, 1997.

8. Dutta-Roy, A. K., Gordon, M. J., Leishman, D. J., Paterson, B. J., Duthie, G. G. and James, W. P. Purification and partial characterization of an alpha-tocopherol-binding protein from rabbit heart cytosol. Mol. Cell. Biochem., 123: 139–144, 1993.

9. Gordon, M. J., Campbell, F. M., Duthie, G. G., and Dutta-Roy, A. K. Characterization of a novel alpha-tocopherol-binding protein from bovine heart cytosol. Arch Biochem. Biophys., 318: 140–146, 1995.

10. Dutta-Roy, A. K. Alpha-tocopherol-binding proteins: purification and characterization. Methods Enzymology 282: 278–297, 1997.

11. Stocker, A., Zimmer, S., Spycher, S. E., and Azzi, A. Identification of a novel cytosolic tocopherol-binding protein: structure, specificity, and tissue distribution. IUBMB Life, 48: 49–55, 1999.

12. Zimmer, S., Stocker, A., Sarbolouki, M. N., Spycher, I S. E., Sassoon, J., and Azzi, A. A novel human tocopherol-associated protein: cloning, in vitro expression, and characterization. J. Boll. Chem., 275: 25672–25680, 2000.

13. Sha, B., Phillips, S. E., Bankaitis, V. A., and Luo, M. Crystal structure of the Saccharomyces cerevisiae phosphatidylinositol-transfer protein. Nature, 391: 506–510, 1998.

14. Shibata, N., Arita, M., Misaki, Y., Dohmae, N., Tako, K., Ono, T., Inoue, K., and Arai, H. Supernatant protein factor, which stimulates the conversion of squalene to lanosterol, is a cytosolic squalene transfer protein and enhances cholesterol biosynthesis. Proc. Natl. Acad. Sci. U.S.A., 98: 2244–2249, 2001.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. An isolated DNA sequence that encodes the amino acid sequence SEQ ID NO: 2.

2. The isolated DNA of claim 1, wherein said DNA comprises the nucleotide sequence SEQ ID NO: 1.

3. A vector comprising the DNA of claim 1 and regulatory elements necessary for the expression of the DNA in a cell.

4. The vector of claim 3, wherein said vector is a plasmid.

5. The vector of claim 3, wherein said vector further encodes an influenza hemagglutin (HA) tag.

6. The vector of claim 3, wherein said vector further encodes a green fluorescent protein.

7. The vector of claim 3, wherein said vector further encodes a glutathione S-transferase (GST) tag.

8. The vector of claim 3, wherein said vector further encodes a polyhistidine (HIS) tag.

9. The vector of claim 3, wherein said vector is a tetracycline regulated (TRE) vector.

10. An isolated host cell transfected with the vector of claim 3, wherein said vector expresses the polypeptide of SEO ID No. 2.

11. The host cell of claim 10, wherein said cell is selected from the group consisting of bacterial cells, plant cells and insect cells.

12. The host cell of claim 11, wherein said bacterial cell is *E. coli*.

* * * * *

UNITED STATES PATENT AND TRADEMARK OFFICE
CERTIFICATE OF CORRECTION

PATENT NO. : 7,045,324 B2  
APPLICATION NO. : 10/419629  
DATED : May 16, 2006  
INVENTOR(S) : Sanders et al.

Page 1 of 1

It is certified that error appears in the above-identified patent and that said Letters Patent is hereby corrected as shown below:

In claim 10, column 28, line 7, delete "SEO ID No." and insert --SEQ ID NO:-- therefor.

Signed and Sealed this

Fifteenth Day of August, 2006

JON W. DUDAS  
*Director of the United States Patent and Trademark Office*

SEQUENCE LISTING

<160> NUMBER OF SEQ ID NOS: 7

<210> SEQ ID NO 1
<211> LENGTH: 1137
<212> TYPE: DNA
<213> ORGANISM: Homo sapiens
<220> FEATURE:
<221> NAME/KEY: cDNA
<223> OTHER INFORMATION: TAP-38 gene sequence

<400> SEQUENCE: 1

```
atgagcggca gagtcggcga tctgagcccc aggcagaagg aggcattggc            50
caagccagaa gcttcgacct gcagaagtcg gaggccatgc tccggaagca           100
tgtggagttc cgaaagcaaa aggacattga caacatcatt agcatggcag           150
cctccagagg tgatccaaca gtatctgtca ctggatgcca agggtctgct           200
gttctcagcc tccaaacagg acctgctgag gaccaagatg ctggatgcca           250
agggtctgct gttctcagcc tccaaacagg acctgctgag gaccaagatg           300
cgggagtgtg agctgcttct gcaagagtgt gcccaccaga ccacaaagtt           350
ggggaggaag gtggagacca tcaccataat ttatgactgc gaggggcttg           400
gcctcaagca tctctggaag cctgctgtgg aggcctatgg agagtttctc           450
```

| | |
|---|---|
| tgcatgtttg aggaaaatta tcccgaaaca ctgaagcgtc tttttgttgt | 500 |
| taaagccccc aaactgtttc ctgtggccta taacctcatc aaaccctttcc | 550 |
| tgagtgagga cactcgtaag aagatcatgg tcctgggagc aaattggaag | 600 |
| gaggttttac tgaaacatat cagccctgac caggtgcctg tggagtatgg | 650 |
| gggcgccatg actgaccctg atggaaaccc caagtgcaaa tccaagatca | 700 |
| actacggggg tgacatcccc aggaagtatt atgtgcgaga ccaggtgaaa | 750 |
| cagcagtatg aacacagcgt gcagatttcc cgtggctcct cccaccaagt | 800 |
| ggagtatgag atcctcttcc ctggctgtgt cctcaggtgg cagtttatgt | 850 |
| cagatggagc ggatgttggt tttgggattt tcctgaagac caagatggga | 900 |
| gagaggcagc gggcagggga gatgacagag gtgctgccca accagaggta | 950 |
| caactcccac ctggtccctg aagatgggac cctcacctgc agtgatcctg | 1000 |
| gcatctatgt cctgcggttt gacaacacct acagcttcat tcatgccaag | 1050 |
| aaggtcaatt tcactgtgga ggtcctgctt ccagacaaag cctcagaaga | 1100 |
| gaagatgaaa cagctggggg caggcacccc gaaataa | 1137 |

<210> SEQ ID NO 2
<211> LENGTH: 378
<212> TYPE: PRT
<213> ORGANISM: Homo sapiens
<220> FEATURE:
<221> NAME/KEY: PEPTIDE
<223> OTHER INFORMATION: P2P polypeptide

<400> SEQUENCE: 2

Met Ser Gly Arg Val Gly Asp Leu Ser Pro Arg Gln Lys Glu Ala
                5                  10                  15

Leu Ala Lys Pro Glu Ala Ser Thr Cys Arg Ser Arg Arg Pro Cys
                20                  25                  30

Ser Gly Ser Met Trp Ser Ser Glu Ser Lys Arg Thr Leu Thr Thr
                35                  40                  45

Ser Leu Ala Trp Gln Pro Pro Glu Val Ile Gln Gln Tyr Leu Ser
                50                  55                  60

Gly Gly Met Cys Gly Tyr Asp Leu Asp Gly Cys Pro Val Trp Tyr
                65                  70                  75

Asp Ile Ile Gly Pro Lys Asp Ala Lys Gly Leu Leu Phe Ser Ala
                80                  85                  90

Ser Lys Gln Asp Leu Leu Arg Thr Lys Met Arg Glu Cys Glu Leu
                95                  100                 105

Leu Leu Gln Glu Cys Ala His Gln Thr Thr Lys Leu Gly Arg Lys
                110                 115                 120

Val Glu Thr Ile Thr Ile Ile Tyr Asp Cys Glu Gly Leu Gly Leu
                125                 130                 135

Lys His Leu Trp Lys Pro Ala Val Glu Ala Tyr Gly Glu Phe Leu
                140                 145                 150

Cys Met Phe Glu Glu Asn Tyr Pro Glu Thr Leu Lys Arg Leu Phe
                155                 160                 165

Val Val Lys Ala Pro Lys Leu Phe Pro Val Ala Tyr Asn Leu Ile
                170                 175                 180

Lys Pro Phe Leu Ser Glu Asp Thr Arg Lys Lys Ile Met Val Leu
                185                 190                 195

-continued

```
Gly Ala Asn Tyr Lys Glu Val Leu Leu Lys His Ile Ser Pro Asp
            200                 205                 210

Gln Val Pro Val Glu Tyr Gly Gly Thr Met Thr Asp Pro Asp Gly
        215                 220                 225

Asn Pro Lys Cys Lys Ser Lys Ile Asn Tyr Gly Gly Asp Ile Pro
    230                 235                 240

Arg Lys Tyr Tyr Val Arg Asp Gln Val Lys Gln Gln Tyr Glu His
245                 250                 255

Ser Val Gln Ile Ser Arg Gly Ser Ser His Gln Val Glu Tyr Glu
            260                 265                 270

Ile Leu Phe Pro Gly Cys Val Leu Arg Trp Gln Phe Met Ser Asp
        275                 280                 285

Gly Ala Asp Val Gly Phe Gly Ile Phe Leu Lys Thr Lys Met Gly
    290                 295                 300

Glu Arg Gln Arg Ala Gly Glu Met Thr Glu Val Leu Pro Asn Gln
305                 310                 315

Arg Tyr Asn Ser His Leu Val Pro Glu Asp Gly Thr Leu Thr Cys
            320                 325                 330

Ser Asp Pro Gly Ile Tyr Val Leu Arg Phe Asp Asn Thr Tyr Ser
        335                 340                 345

Phe Ile His Ala Lys Lys Val Asn Phe Thr Val Glu Val Leu Leu
    350                 355                 360

Pro Asp Lys Ala Ser Glu Glu Lys Met Lys Gln Leu Gly Ala Gly
365                 370                 375

Thr Pro Lys
```

<210> SEQ ID NO 3
<211> LENGTH: 1212
<212> TYPE: DNA
<213> ORGANISM: Homo sapiens
<220> FEATURE:
<221> NAME/KEY: cDNA
<223> OTHER INFORMATION: TAP-46 gene sequence

<400> SEQUENCE: 3

| | |
|---|---|
| atgagcggca gagtcggcga tctgagcccc aggcagaagg aggcattggc | 50 |
| caagtttcgg gagaatgtcc aggatgtgct gccggccctg ccgaatccag | 100 |
| atgactattt tctcctgcgt tggctccgag ccagaagctt cgacctgcag | 150 |
| aagtcggagg ccatgctccg gaagcatgtg gagttccgaa agcaaaagga | 200 |
| cattgacaac atcattagct ggcagcctcc agaggtgatc aacagtatc | 250 |
| tgtcactgga tgccaagggt ctgctgttct cagcctccaa acaggacctg | 300 |
| ctgaggacca agatgctgga tgccaagggt ctgctgttct cagcctccaa | 350 |
| acaggacctg ctgaggacca agatgcggga gtgtgagctg cttctgcaag | 400 |
| agtgtgccca ccagaccaca aagttgggga ggaaggtgga gaccatcacc | 450 |
| ataatttatg actgcgaggg gcttggcctc aagcatctct ggaagcctgc | 500 |
| tgtggaggcc tatggagagt ttctctgcat gttttgaggaa aattatcccg | 550 |
| aaacactgaa gcgtcttttt gttgttaaag ccccccaaact gtttcctgtg | 600 |
| gcctataacc tcatcaaacc cttcctgagt gaggacactc gtaagaagat | 650 |
| catggtcctg ggagcaaatt ggaaggaggt tttactgaaa catatcagcc | 700 |
| ctgaccaggt gcctgtggag tatgggggcg ccatgactga ccctgatgga | 750 |

-continued

| | |
|---|---|
| aaccccaagt gcaaatccaa gatcaactac gggggtgaca tccccaggaa | 800 |
| gtattatgtg cgagaccagg tgaaacagca gtatgaacac agcgtgcaga | 850 |
| tttcccgtgg ctcctcccac caagtggagt atgagatcct cttccctggc | 900 |
| tgtgtcctca ggtggcagtt tatgtcagat ggagcggatg ttggttttgg | 950 |
| gattttcctg aagaccaaga tgggagagag cagcgggca ggggagatga | 1000 |
| cagaggtgct gcccaaccag aggtacaact cccacctggt ccctgaagat | 1050 |
| gggaccctca cctgcagtga tcctggcatc tatgtcctgc ggtttgacaa | 1100 |
| cacctacagc ttcattcatg ccaagaaggt caatttcact gtggaggtcc | 1150 |
| tgcttccaga caaagcctca gaagagaaga tgaaacagct gggggcaggc | 1200 |
| accccgaaat aa | 1212 |

<210> SEQ ID NO 4
<211> LENGTH: 403
<212> TYPE: PRT
<213> ORGANISM: Homo sapiens
<220> FEATURE:
<221> NAME/KEY: PEPTIDE
<223> OTHER INFORMATION: TAP-46 polypeptide

<400> SEQUENCE: 4

Met Ser Gly Arg Val Gly Asp Leu Ser Pro Arg Gln Lys Glu Ala
            5                   10                  15

Leu Ala Lys Phe Arg Glu Asn Val Gln Asp Val Leu Pro Ala Leu
            20                  25                  30

Pro Asn Pro Asp Asp Tyr Phe Leu Leu Arg Trp Leu Arg Ala Arg
            35                  40                  45

Ser Phe Asp Leu Gln Lys Ser Glu Ala Met Leu Arg Lys His Val
            50                  55                  60

Glu Phe Arg Lys Gln Lys Asp Ile Asp Asn Ile Ile Ser Trp Gln
            65                  70                  75

Pro Pro Glu Val Ile Gln Gln Tyr Leu Ser Gly Gly Met Cys Gly
            80                  85                  90

Tyr Asp Leu Asp Gly Cys Pro Val Trp Tyr Asp Ile Ile Gly Pro
            95                  100                 105

Leu Asp Ala Lys Gly Leu Leu Phe Ser Ala Ser Lys Gln Asp Leu
            110                 115                 120

Leu Arg Thr Lys Met Arg Glu Cys Glu Leu Leu Gln Glu Cys
            125                 130                 135

Ala His Gln Thr Thr Lys Leu Gly Arg Lys Val Glu Thr Ile Thr
            140                 145                 150

Ile Ile Tyr Asp Cys Glu Gly Leu Gly Leu Lys His Leu Trp Lys
            155                 160                 165

Pro Ala Val Glu Ala Tyr Gly Glu Phe Leu Cys Met Phe Glu Glu
            170                 175                 180

Asn Tyr Pro Glu Thr Leu Lys Arg Leu Phe Val Val Lys Ala Pro
            185                 190                 195

Lys Leu Phe Pro Val Ala Tyr Asn Leu Ile Lys Pro Phe Leu Ser
            200                 205                 210

Glu Asp Thr Arg Lys Lys Ile Met Val Leu Gly Ala Asn Trp Lys
            215                 220                 225

Glu Val Leu Leu Lys His Ile Ser Pro Asp Gln Val Pro Val Glu
            230                 235                 240

```
Tyr Gly Gly Thr Met Thr Asp Pro Asp Gly Asn Pro Lys Cys Lys
            245                 250                 255

Ser Lys Ile Asn Tyr Gly Gly Asp Ile Pro Arg Lys Tyr Tyr Val
            260                 265                 270

Arg Asp Gln Val Lys Gln Gln Tyr Glu His Ser Val Gln Ile Ser
            275                 280                 285

Arg Gly Ser Ser His Gln Val Glu Tyr Glu Ile Leu Phe Pro Gly
            290                 295                 300

Cys Val Leu Arg Trp Gln Phe Met Ser Asp Gly Ala Asp Val Gly
            305                 310                 315

Phe Gly Ile Phe Leu Lys Thr Lys Met Gly Glu Arg Gln Arg Ala
            320                 325                 330

Gly Glu Met Thr Glu Val Leu Pro Asn Gln Arg Tyr Asn Ser His
            335                 340                 345

Leu Val Pro Glu Asp Gly Thr Leu Thr Cys Ser Asp Pro Gly Ile
            350                 355                 360

Tyr Val Leu Arg Phe Asp Asn Thr Tyr Ser Phe Ile His Ala Lys
            365                 370                 375

Lys Val Asn Phe Thr Val Glu Val Leu Leu Pro Asp Lys Ala Ser
            380                 385                 390

Glu Glu Lys Met Lys Gln Leu Gly Ala Gly Thr Pro Lys
            395                 400
```

<210> SEQ ID NO 5
<211> LENGTH: 21
<212> TYPE: DNA
<213> ORGANISM: artificial sequence
<220> FEATURE:
<221> NAME/KEY: primer_bind
<223> OTHER INFORMATION: TAP-38 sense oligonucleotide

<400> SEQUENCE: 5
atgagcggca gagtcggcga t                                      21

<210> SEQ ID NO 6
<211> LENGTH: 21
<212> TYPE: DNA
<213> ORGANISM: artificial sequence
<220> FEATURE:
<221> NAME/KEY: primer_bind
<223> OTHER INFORMATION: TAP-38 antisense oligonucleotide

<400> SEQUENCE: 6
ttatttcggg gtgcctgccc c                                      21

<210> SEQ ID NO 7
<211> LENGTH: 57
<212> TYPE: DNA
<213> ORGANISM: artificial sequence
<220> FEATURE:
<221> NAME/KEY: primer_bind
<223> OTHER INFORMATION: TAP-38 sense oligonucleotide encoding HA-tag

<400> SEQUENCE: 7
cgcgaattca tgtatgatgt tcctgattat gctagcctca gcggcagagt        50
cggcgat                                                      57